(12) United States Patent
Fallah (10) Patent No.: US 7,381,191 B2
(45) Date of Patent: Jun. 3, 2008

(54) SINUS NERVE LOCATOR

(76) Inventor: Afshin Al Fallah, 2419 Buckingham La., Los Angeles, CA (US) 90077

( * ) Notice: Subject to any disclaimer, the term of this patent is extended or adjusted under 35 U.S.C. 154(b) by 0 days.

(21) Appl. No.: 11/378,467

(22) Filed: Mar. 20, 2006

(65) Prior Publication Data

US 2006/0210950 A1    Sep. 21, 2006

Related U.S. Application Data

(60) Provisional application No. 60/663,581, filed on Mar. 21, 2005.

(51) Int. Cl.
*A61B 5/103*    (2006.01)
*A61C 19/04*    (2006.01)
(52) U.S. Cl. .................. 600/590; 600/557; 433/72
(58) Field of Classification Search .......... 433/72, 433/75–76; 33/553–554; 600/590, 557; 600/587, 433, 72, 600
See application file for complete search history.

(56) References Cited

U.S. PATENT DOCUMENTS

| | | | |
|---|---|---|---|
| 3,672,058 A | 6/1972 | Nikoghossian | |
| 3,722,100 A | 3/1973 | Weisman et al. | |
| 4,273,117 A * | 6/1981 | Neuhauser | 606/80 |
| 4,462,802 A | 7/1984 | Sekiya | |
| 4,964,412 A | 10/1990 | Kelly | |
| 5,176,516 A * | 1/1993 | Koizumi | 433/72 |
| 5,928,238 A * | 7/1999 | Scarborough et al. | 606/79 |
| 5,967,777 A * | 10/1999 | Klein et al. | 433/75 |
| 5,989,025 A * | 11/1999 | Conley | 433/76 |
| 6,234,977 B1 | 5/2001 | Christy | |
| 6,379,148 B1 | 4/2002 | Chen | |
| 7,014,461 B2 * | 3/2006 | Weinstein | 433/76 |
| 7,079,883 B2 * | 7/2006 | Marino et al. | 600/373 |
| 2003/0082497 A1 * | 5/2003 | Kastenbaum | 433/144 |
| 2003/0170587 A1 | 9/2003 | Augthun et al. | |
| 2004/0259051 A1 * | 12/2004 | Brajnovic | 433/75 |

* cited by examiner

*Primary Examiner*—John J Wilson
(74) *Attorney, Agent, or Firm*—Christopher Wood; Wood & Eisenberg, PLLC (57) ABSTRACT

Dental devices in the form of a temporary implant for securing a rubber dam clamp, and a nerve locator for aiding a dental surgeon during oral surgery on a patient.

2 Claims, 14 Drawing Sheets

SINUS NERVE LOCATOR

CROSS-REFERENCE TO RELATED APPLICATIONS

This application claims the benefit of priority from U.S. Provisional Patent Application Ser. No. 60/663,581, filed Mar. 21, 2005, which is herein incorporated by reference in its entirety.

STATEMENT REGARDING FEDERALLY SPONSORED RESEARCH OR DEVELOPMENT

Not Applicable.

FIELD OF THE INVENTION

This invention relates generally to dental devices. More specifically, this invention relates to a temporary implant for securing a rubber dam clamp, and a nerve locator for aiding a dental surgeon during oral surgery on a patient.

BACKGROUND OF THE INVENTION

Operating on dental patients presents numerous problems and issues for both the patient and professional provider, such as a dentist, dental surgeon, or oral surgeon. Thus, there remains a strong need for dental devices that aid the professional provider in performing oral surgery.

The Applicant is unaware of inventions or patents, taken either singly or in combination, which are seen to describe the instant invention as claimed.

SUMMARY OF THE INVENTION

This invention is directed to dental devices in the form of a temporary implant for securing a rubber dam clamp, and a nerve locator for aiding a dental surgeon during oral surgery on a patient.

BRIEF DESCRIPTION OF THE DRAWINGS

Similar reference characters denote corresponding features consistently throughout the attached drawings.

DETAILED DESCRIPTION OF THE PREFERRED EMBODIMENTS

This invention is directed to dental devices in the form of a temporary implant for securing a rubber dam clamp, and a nerve locator for aiding a dental surgeon during oral surgery on a patient.

The temporary implant and nerve locator devices of the present invention are indicated generally by the numerals 100 and 1000, respectively.

Figure 1:
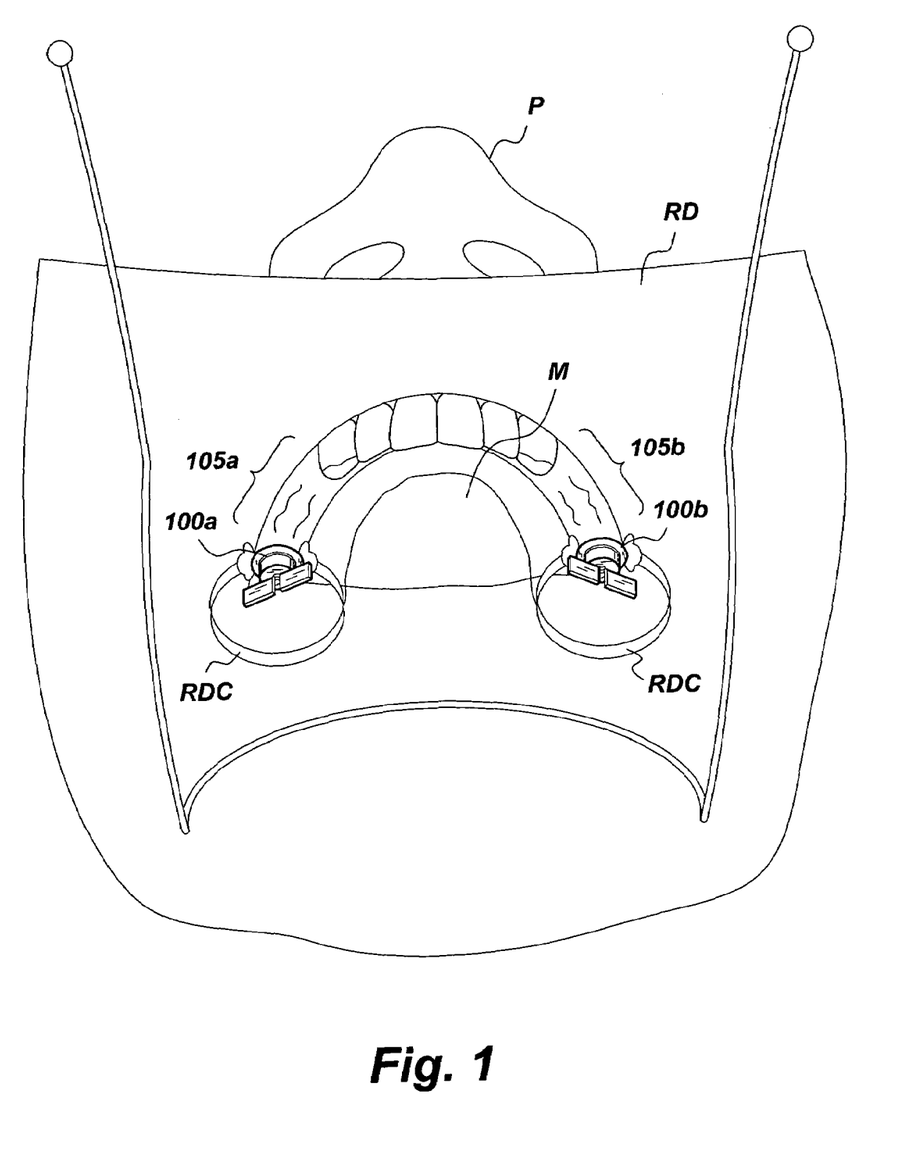
FIG. 1 is an environmental, perspective view of two temporary implant devices fitted inside a patient's mouth, according to one aspect of the invention.

FIG. 1 shows a perspective environmental view of two temporary implant devices 100 (actually represented by alpha-numeric labels "100*a*" and "100*b*") respectively screwed into the upper jaw (maxilla) of a patient P to provide anchor points for rubber dam clamps RDC, which in turn provide anchor points to secure a rubber dam RD to isolate areas of the mouth M such as toothless areas 105*a* and 105*b*. It should be understood that the temporary implant device 100 could be screwed into the bone of the lower jaw (mandible) in addition to the upper jaw (maxilla).

For example, the temporary implant 100 enables a professional provider, such as a dentist, dental surgeon, or oral surgeon, to isolate a toothless area of the maxilla or mandible of a patient's mouth M. Specifically, the temporary implant 100 acts as a platform or anchor point on which to secure a rubber dam clamp RDC, which in turn is used to secure a rubber dam RD inside a patient's mount M.

Figure 2:
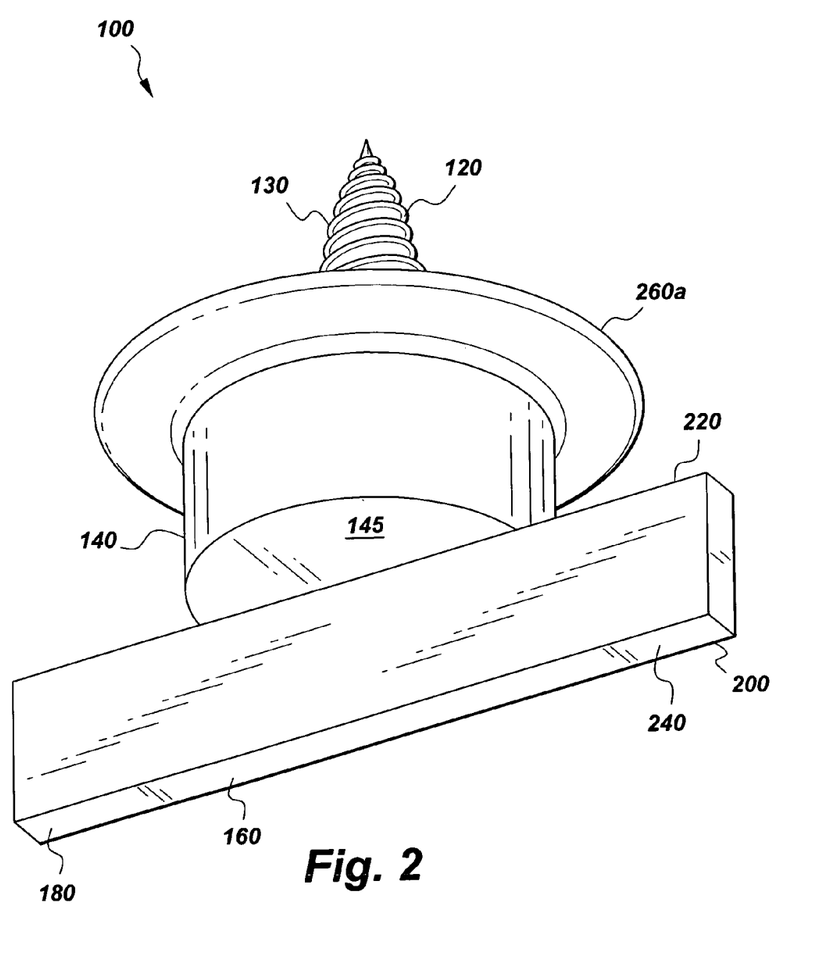
FIG. 2 is a perspective view of a temporary implant device, according to the invention.

Referring to FIG. 2, a temporary implant device 100 is shown comprising of a drill section 120 of conical shape, a rubber dam clamp grip section 140 having opposite ends 280 and 300 (see FIG. 5), and an optional torque delivery member 160. Torque delivery member 160 includes opposite ends 180 and 200, and upper and lower surfaces 220 and 240. The temporary implant 100 further comprises an optional rim 260*a*. The grip section 140 is shown located between the optional rim 260*a* and upper surface 220 of torque delivery member 160. With this design, it is a simple matter for a dentist to fit a rubber dam clamp RDC between the rim 260*a* and upper surface 220 of torque delivery member 160. The optional rim 260*a* also helps protect the patient's gum from, for example, inadvertent movement of the rubber dam clamp RDC during a dental procedure. The rubber dam clamp RDC is typically used to secure a rubber dam RD, which in turn is typically used by a dentist to isolate a section of a patient's mouth M.

It should be understood that the grip section 140 can have a variety of cross-sectional shapes, such as a circular shape to provide a cylindrical 3D shape as shown, for example, in FIG. 2. However, the grip section 140 can have an oval or polygonal cross-section such as, but not limited to, a regular hexagonal, irregular hexagonal cross-section, or a combination of such shapes. The grip section 140 can have a rectangular or square cross-section.

Still referring to FIG. 2, the temporary implant 100 is rotated by applying torque to the torque delivery member 160, or at ends 180 and 200 thereof. Contacting the drill section 120 with the lower (mandible) or upper jaw (maxilla) and rotating the temporary implant 100 causes the drill section 120 to drill into the jaw bone. The drill section 120 includes an external cutting thread 130.

Once secured in the patient's jaw, the temporary implant 100 allows a dentist to attach a rubber dam clamp RDC to the rubber dam clamp grip section 140. The temporary implant 100 is removed by applying opposite torque to the torque delivery member 160.

The implant 100 typically works in conjunction with a rubber dam clamp RDC. Thus, the temporary implant 100 enables a rubber dam clamp RDC to secure a rubber dam RD in place inside a patient's mouth M to isolate an area of the maxilla or mandible, such as, but not limited to, a toothless section (represented by alpha-numeral label 105*a* or 105*b* in FIG. 1). Specifically, it can be difficult to attach a rubber dam clamp RDC to a toothless section of the maxilla or mandible. The temporary implant 100 solves this problem by providing a rubber dam clamp grip section 140.

Figure 3A:
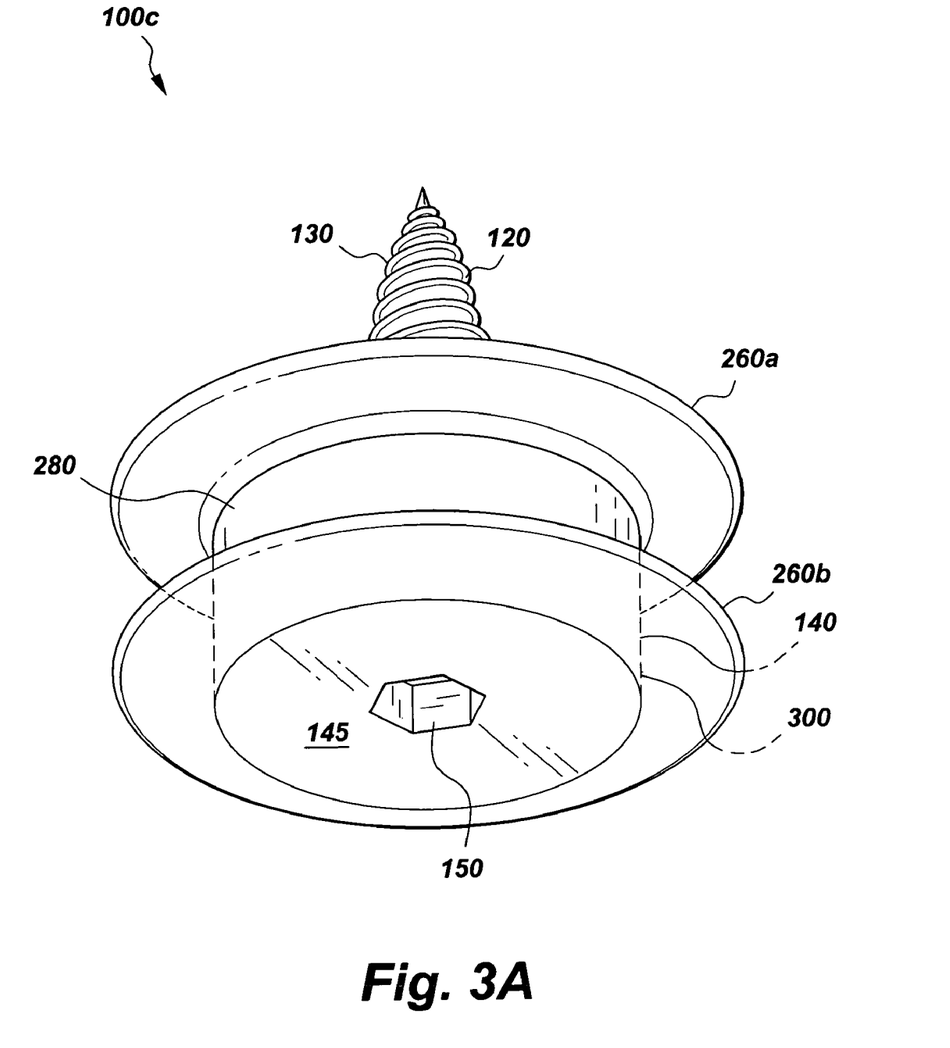
FIG. 3A is a perspective view of a further temporary implant device, according to the invention.

Referring to FIG. 3A, which shows another embodiment of the invention, the temporary implant 100 (represented by alpha-numeral label "100*c*") lacks the optional torque delivery member 160. Instead, the temporary implant 100*c* comprises two rim members 260*a* and 260*b* respectively wrapped around the opposite ends 280 and 300 of grip section 140. The grip section 140 comprises a bottom surface 145. A female insert member 150 is recessed into the bottom surface 145 and is shaped to accommodate the male end of a complementary shaped torque delivery tool (not shown). The female insert 150 can have any suitable shape, such as, but not limited to: regular or irregular polygonal shape, rectangular, square, regular hexagonal shape, irregular hexagonal shape or a combination of such shapes.

Figure 3B:
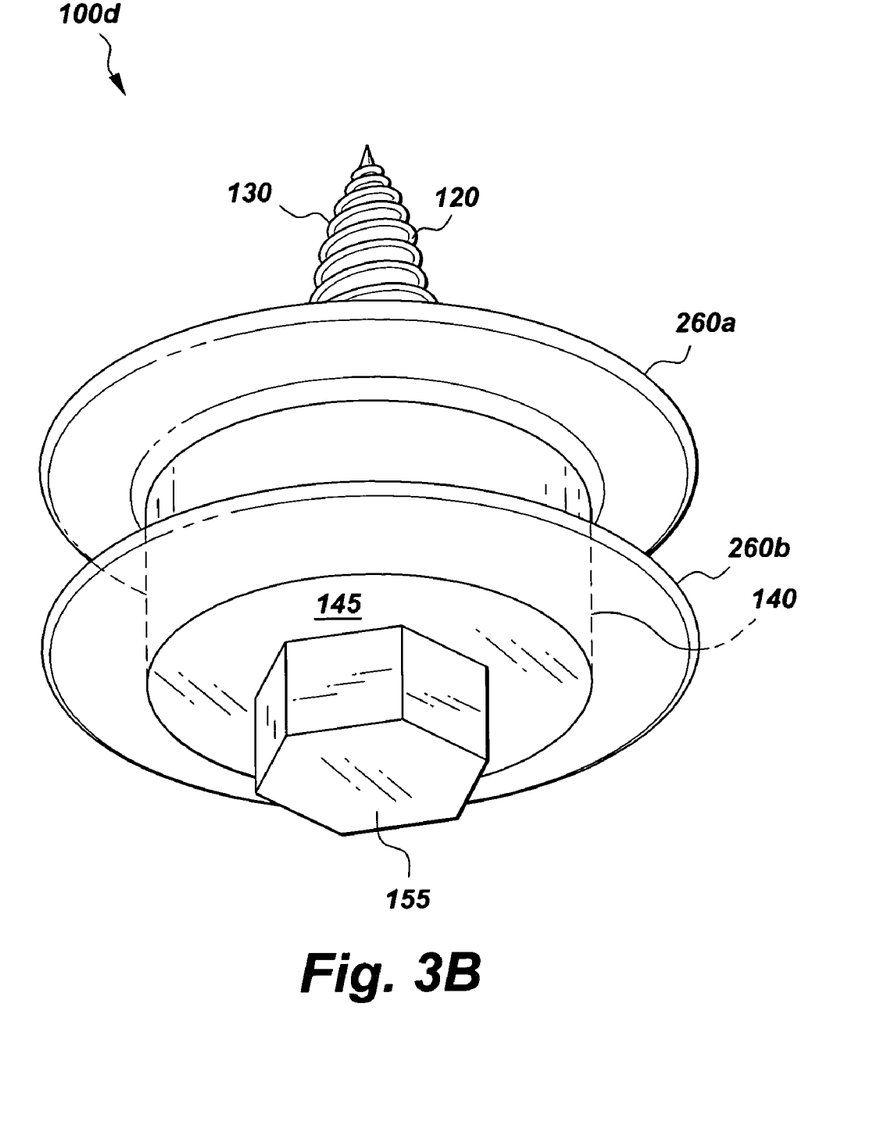
FIG. 3B is a perspective view of another temporary implant device, according to the invention.
Figure 3C:
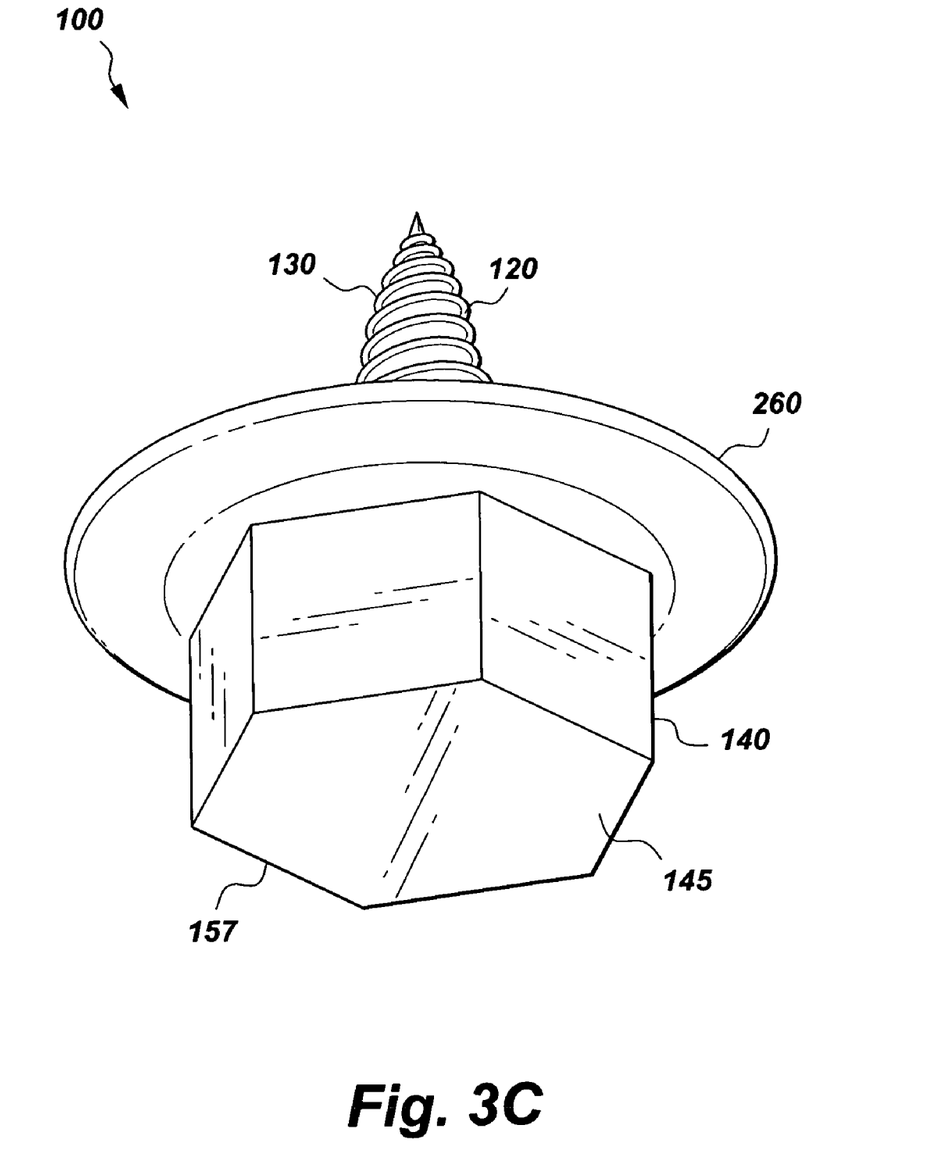
FIG. 3C is a perspective view of another temporary implant device, according to the invention.
Figure 3D:
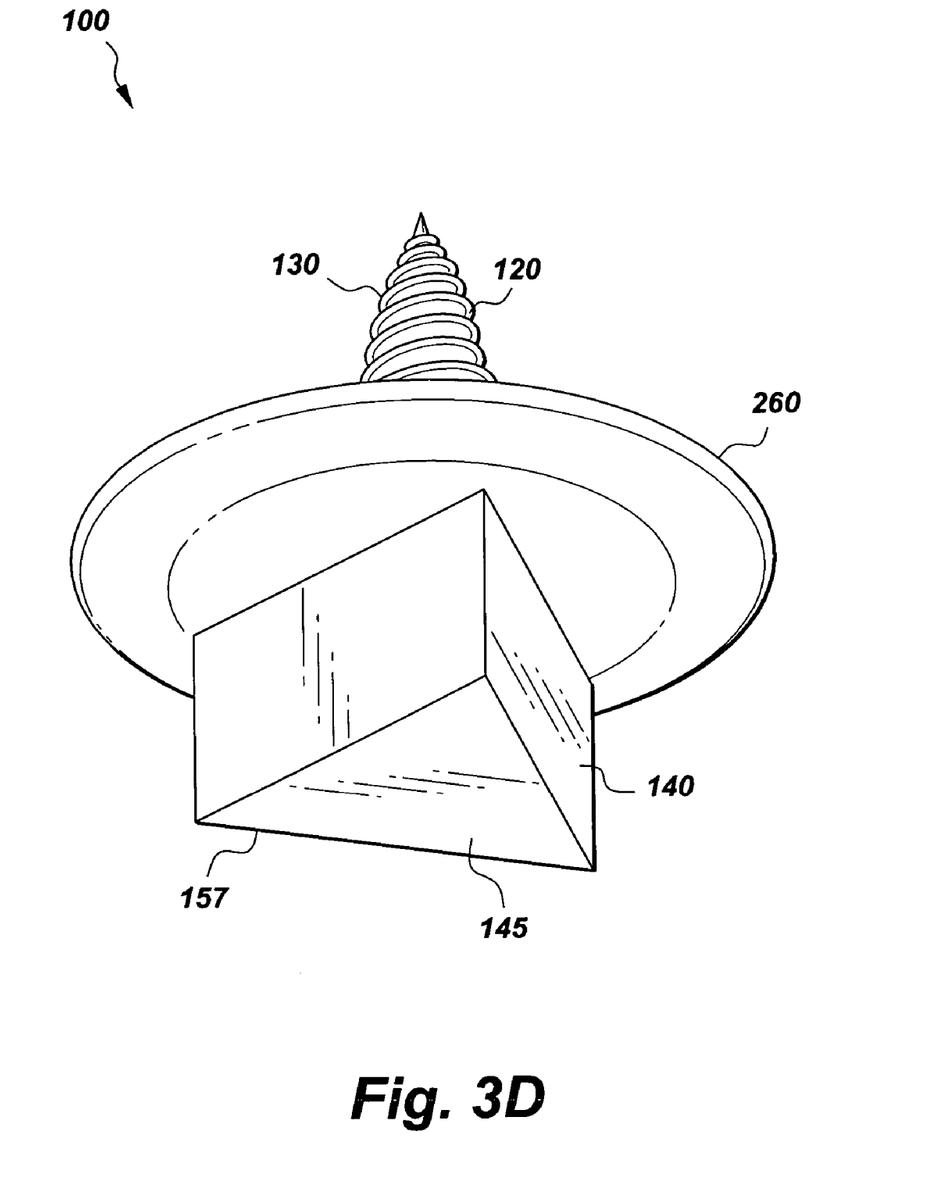
FIG. 3D is a perspective view of another temporary implant device, according to the invention.

Referring to FIG. 3B, which shows another embodiment of the invention, the temporary implant 100 (represented by alpha-numeral label "100*d*") comprises a male plug 155, which protrudes from the bottom surface 145, and is shaped to fit, for example, a hexagonally shaped female socket on the end of a torque delivery tool (not shown). It should be understood that the male plug member 155 could adopt any suitable shape. For example, the male plug member 155 is at least one shape selected from the group: regular polygonal shape, irregular polygonal shape, rectangular, square, regular hexagonal shape, and irregular hexagonal shape.

Figure 4:
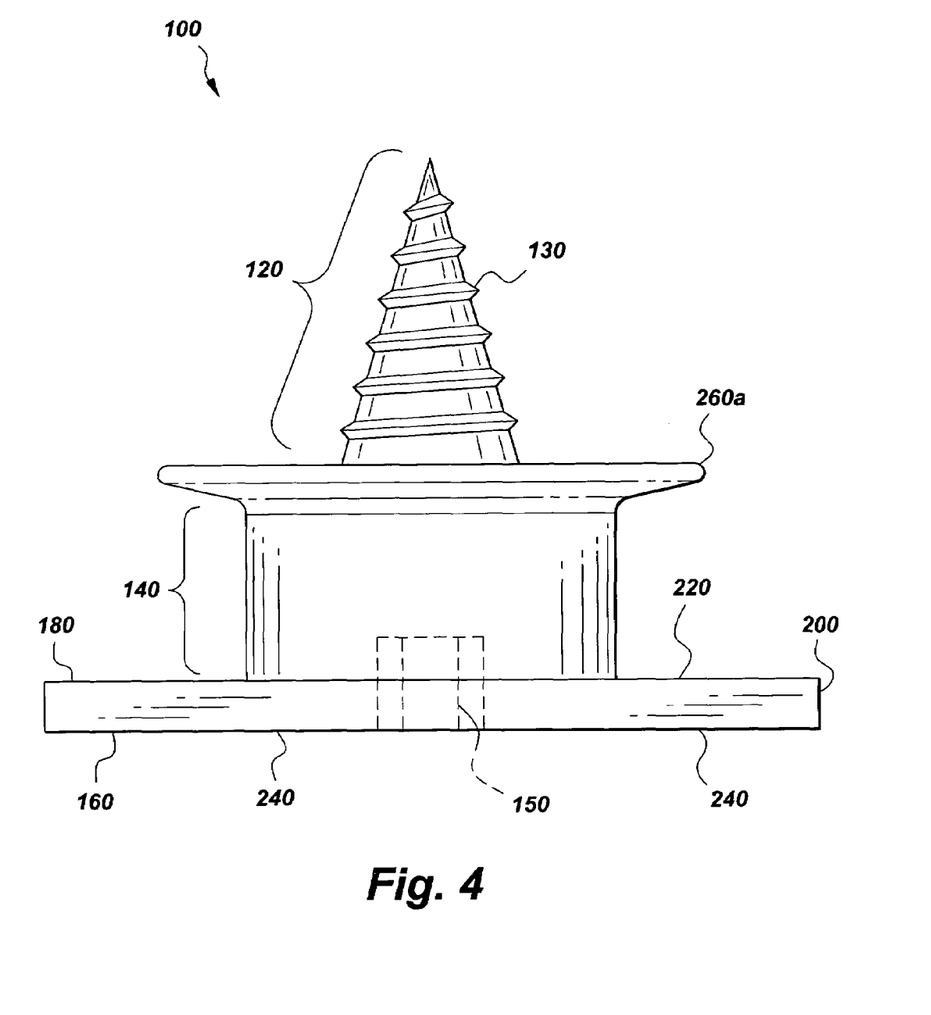
FIG. 4 is a side view of another temporary implant device, according to the invention.

In FIG. 4 the optional torque delivery member 160 is combined with a female insert 150 shaped to accommodate the male end of a complementary shaped torque delivery tool (not shown).

Figure 5:
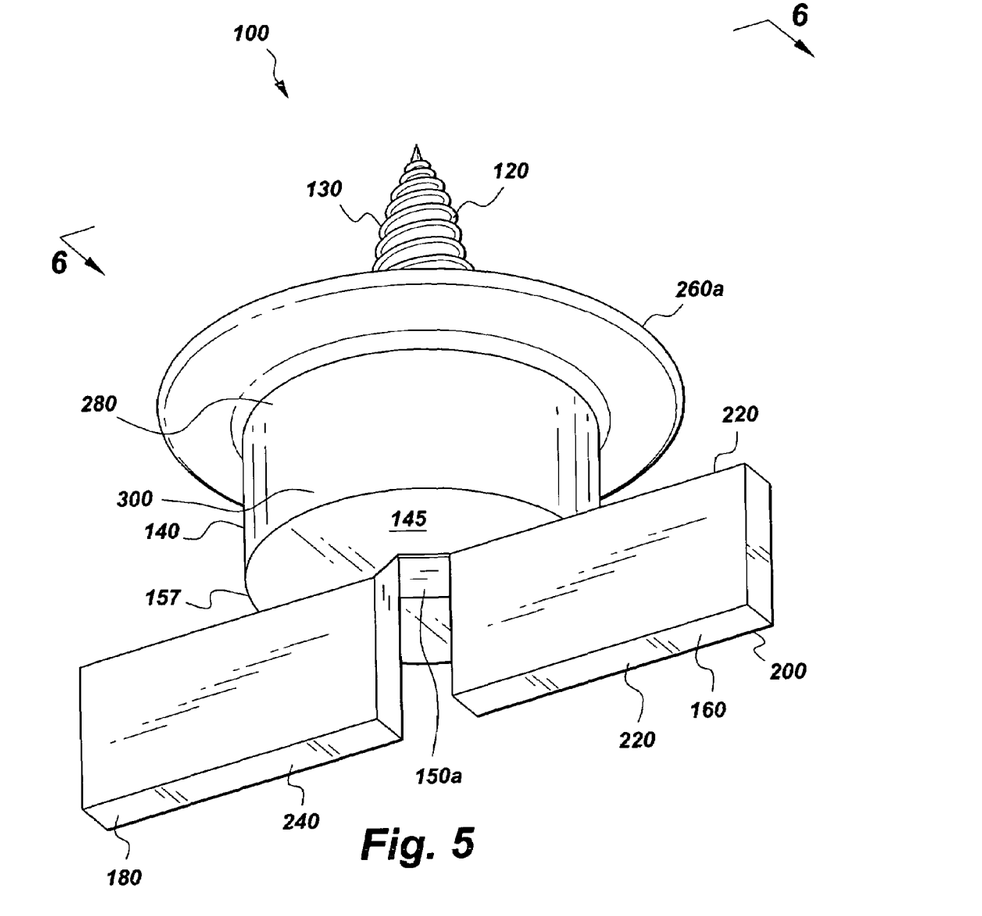
FIG. 5 is a perspective view of another temporary implant device, according to the invention.

FIG. 5 shows a perspective view of the optional torque delivery member 160 and female insert 150*a* shaped to accommodate the male end of a complementary shaped torque delivery tool (not shown). The bottom surface 145 of grip section 140 comprises perimeter 157, and opposite ends 280 and 300.

Figure 6:
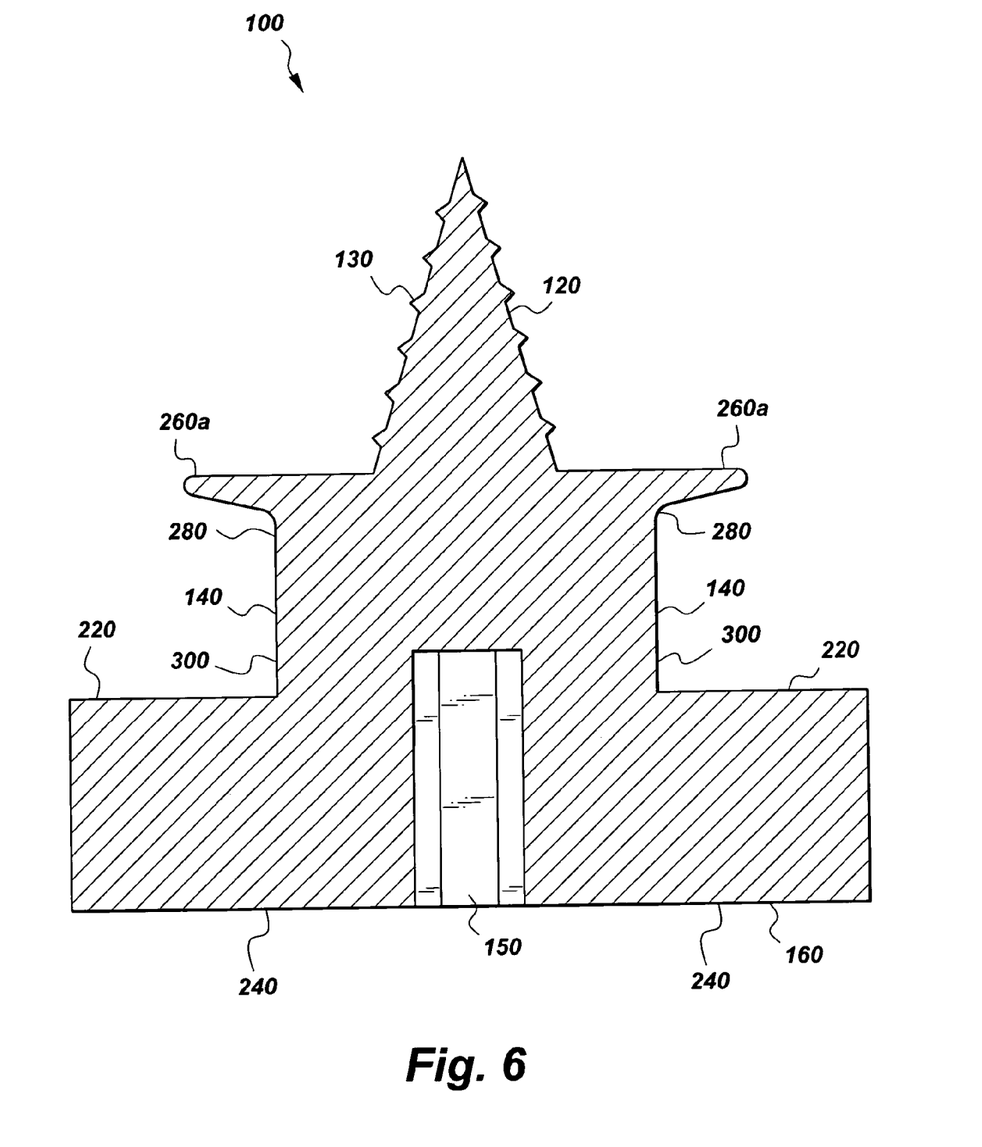
FIG. 6 is a cross-section view of the temporary implant device of FIG. 5.

FIG. 6 shows a cross-section of the temporary implant device of FIG. 5. It should be understood that the dimensions of the various constituent parts of the device 100 can vary. The only limitation on the dimensions of device 100 is that device 100 should fit comfortably inside a patient's mouth and the drill section 120 should be of sufficient depth to enable the device 100 to be affixed to the bone of the maxilla or mandible.

Referring generally to FIGS. 7 through 11, Essentially, the sinus nerve locator 1000 should be of a size that allows a competent medical professional to rotate and hence drill the device 1000 into a patient's mouth bone, in an area of the mouth that lacks teeth. The terms "patient" and "person" are regarded herein as equivalent terms. The terms "competent medical professional" and "dentist" are regarded herein as equivalent terms. With regard to dimensions, the sinus nerve locator 1000 should be small enough to fit inside a patient's mouth and large enough to drill into a patients bone (such as tooth free spot on the mandible) to locate the patient's sinus nerve.

Figure 7:
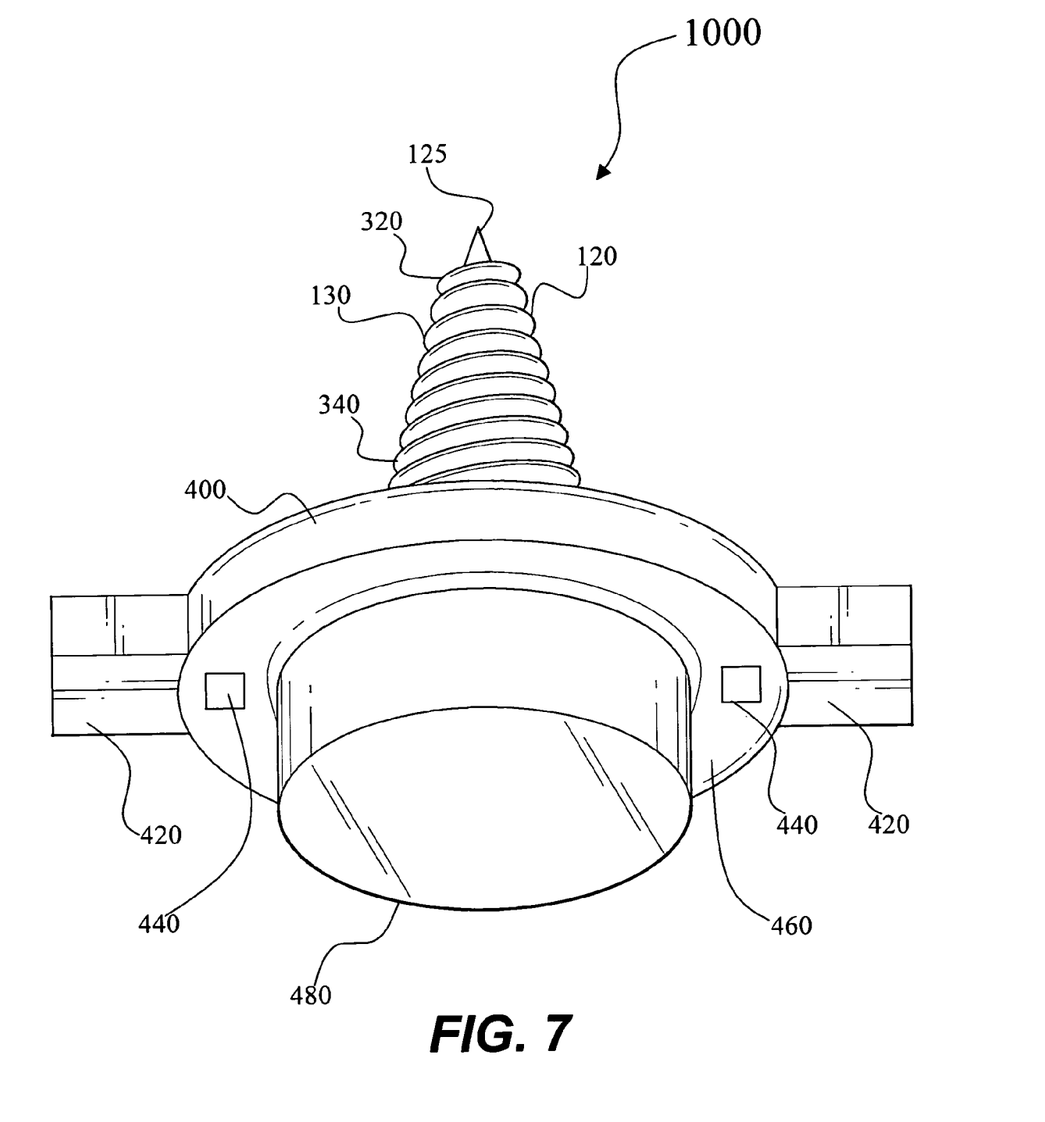
FIG. 7 shows a perspective view of a sinus nerve locator, according to the invention.
Figure 8:
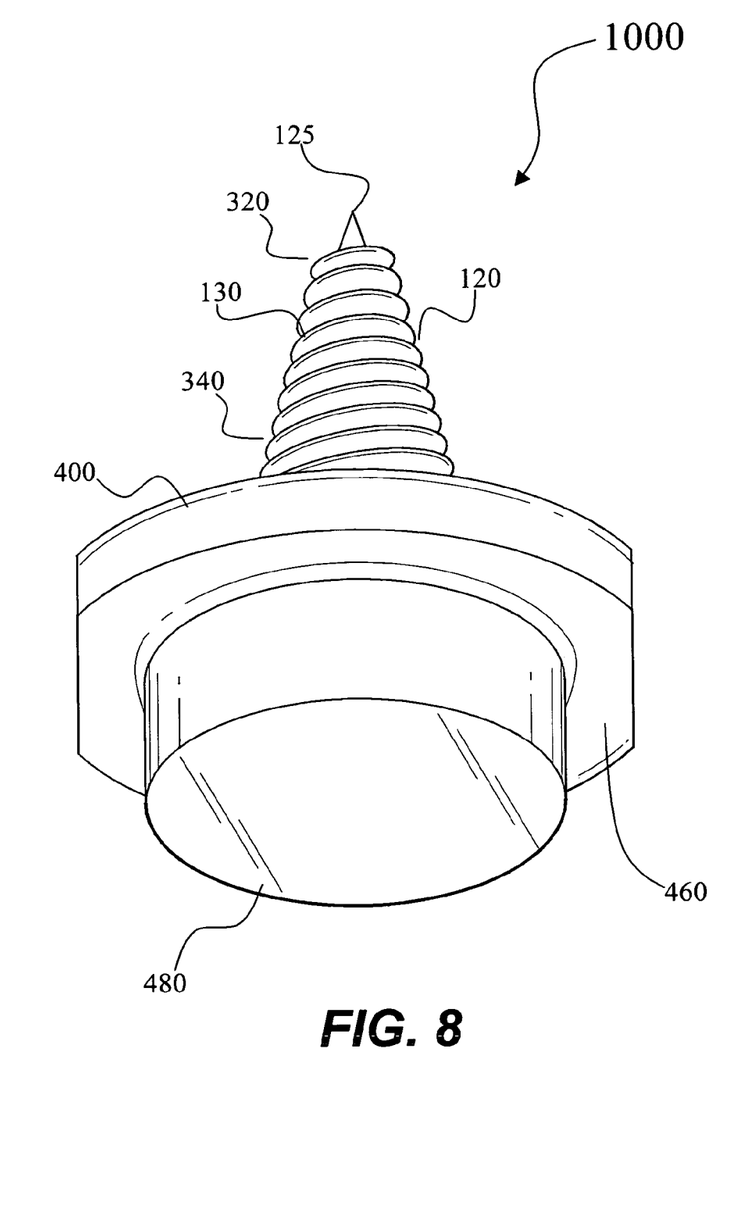
FIG. 8 shows a perspective view of a sinus nerve locator, according to the invention.
Figure 9:
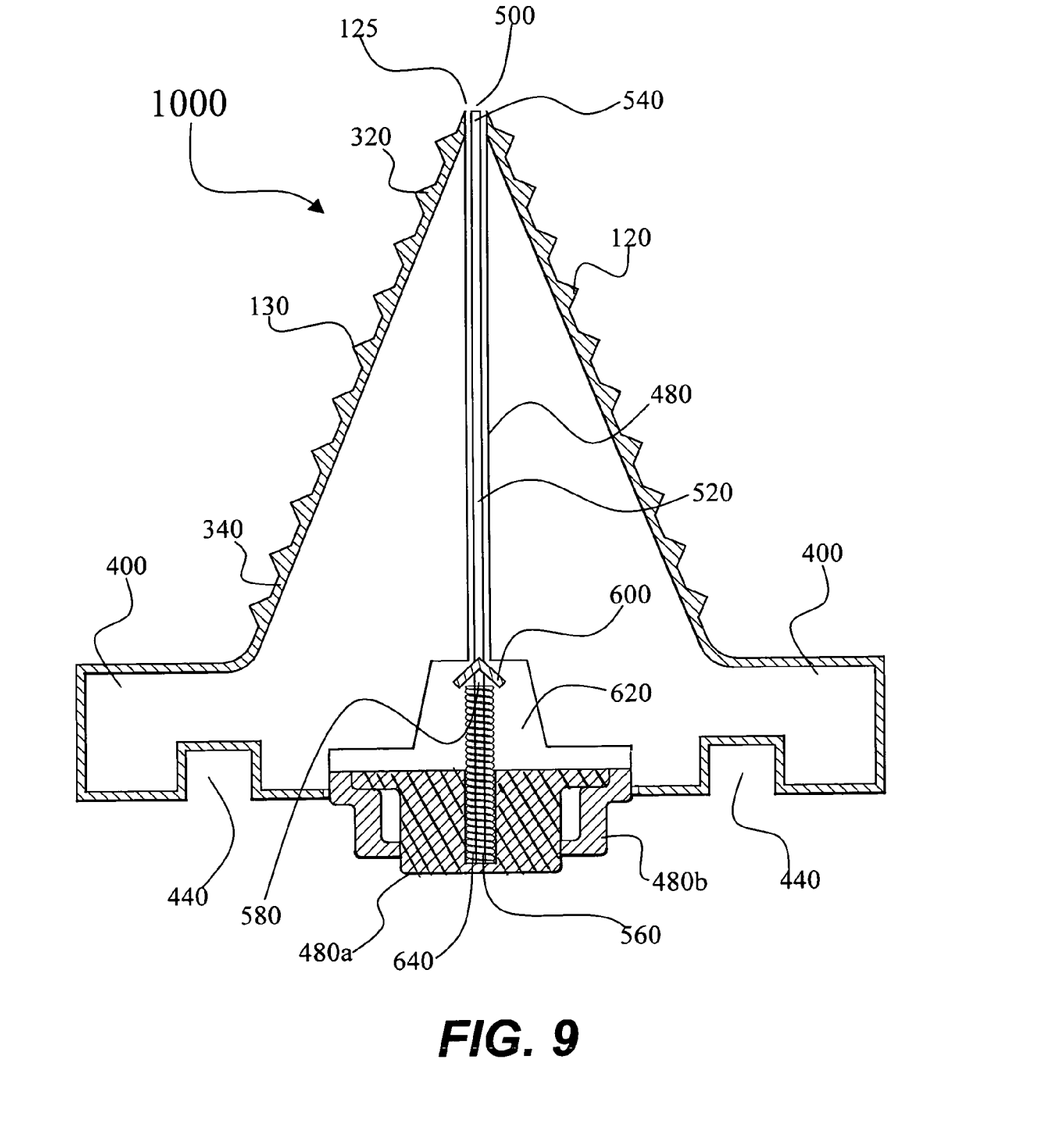
FIG. 9 shows a cross-section view of a sinus nerve locator, according to the invention.
Figure 11:
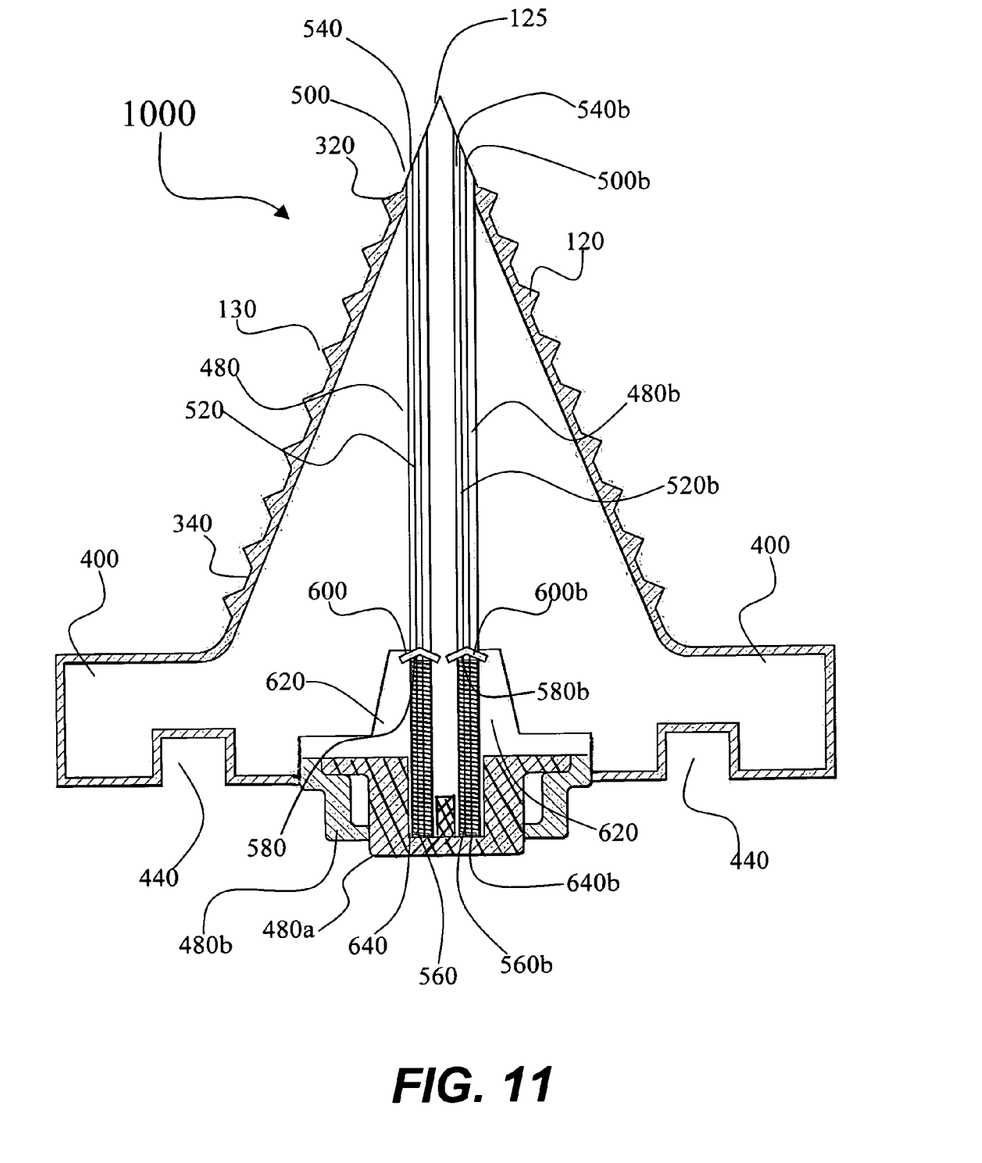
FIG. 11 shows a cross-section view of a sinus nerve locator, according to the invention.

Referring to FIG. 7, the sinus nerve locator 1000 includes a drill section 120 having top 320 and bottom 340 ends, and drill tip 125. The sinus nerve locator 1000 includes a base member 400, which is connected to the bottom 340 of drill section 120. The base member 400 can have an overall polygonal shape around which a wrench of complementary polygonal shape can fit and be used to turn the base member 400 and hence drill section 120. A spring housing 480 is fitted into the bottom 460 of the base member 400. It should be understood that the spring housing 480 can either be screwed in with respect to chamber 620 or slide in and out with respect to chamber 620. The spring housing 480 can comprise two parts 480*a* and 480*b* (as shown in FIGS. 9 and 11), wherein part 480*a* slides in and out under the pressure of a dentist's finger or thumb. The operator has the flexibility of screwing the sinus nerve locator 1000 as much as necessary until the pressing of the spring housing 480*a* indicates that the tip 125 of the sinus nerve locator 1000 has reached the soft sinus membrane or the soft nerve tissue.

The chamber 620 has an interior space to accommodate up and down movement of the spring housing 480.

The sinus nerve locator 1000 can be fitted with optional finger size handles 420 connected to, or integral with, base member 400. The optional finger size handles 420 allow a dentist to rotate the base member 400 and hence the whole device 1000 including drill section 120 to drill the sinus nerve locator 1000 into a patient's bone or tooth. It will be understood by a person of ordinary skill in the art that any suitable method or means can be used to rotate the base member 400. For example, a dentist could wear non-slip gloves to firmly grip the base member 400 of general circular cross section and absent grip slots 440 or any other torque assisting modification to rotate the sinus nerve locator 1000.

Optional grip slots 440 can form part of the lower surface 460 of base member 400. A complementary pronged tool can be inserted into the optional grip slots 440 to rotate the sinus nerve locator 1000. In addition, the base member 400 can be shaped (see FIG. 8) such that a ratchet wrench can be fitted around the base member 400.

Referring to FIG. 9, which shows a cross-section view of the sinus nerve locator 1000 of FIG. 7. The drill section 120 has a generally elongated first hollow bore 480. The first hollow bore 480 is disposed lengthwise inside drill section 120 from the top 320 and bottom 340 ends of said drill section 120. The first hollow bore, 480 defines a first aperture 500 in the top 320 of drill section 120.

Figure 10:
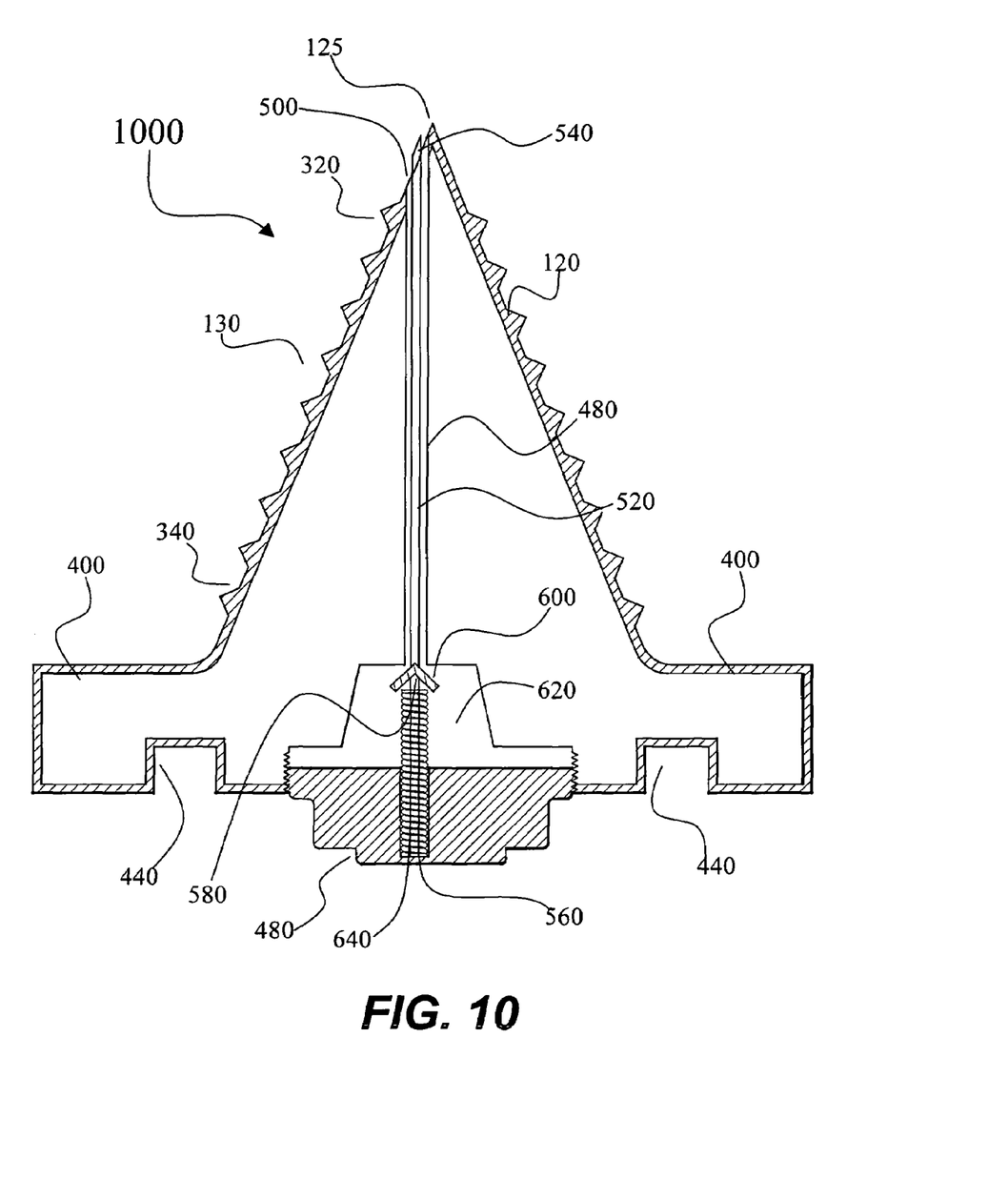
FIG. 10 shows a cross-section view of a sinus nerve locator, according to the invention.

Still referring to FIG. 9, the sinus nerve locator 1000 further includes a generally elongated first rod 520, said first rod 520 at least partly located inside said first hollow bore 480, said first rod 520 having first 540 and second 560 opposite ends. The bottom part 580 of the first rod 520 defines a first flange 600. The first flange 600 is located in a chamber 620. A first spring 640 is mounted beneath first flange 600 and around the bottom part 580 of first rod 520. The spring housing 480 ensures that the first spring 640 applies an upward force to the first flange 600 and hence to the rod 520. The spring housing 480 is screwed into base member 400 as shown in FIG. 10. An operator, such as a dental surgeon, can adjust the upward force delivered by first spring 640 to the first rod 520 by rotating the spring housing 480 to screw into or outward from base member 400. Thus, the first rod 520 is coaxed to emerge through and outward from first aperture 500 in the drill tip 125. In this embodiment the first aperture 500, and hence the first end 540 of rod 520, is centered on the drill tip 125 of drill section 120.

In FIG. 10, the first aperture 500, first hollow bore 480, first rod 520 are all slightly off center with respect to the tip 125 of the drill section 120.

In FIG. 11, the device 1000 is similar to that shown in FIG. 10, except that the device 1000 further includes an off-center second bore 480b, and a second rod 520b having first 540b and second 560b opposite ends along with bottom section 580b. The top part 320 of drill section 120 further defines a second off-center aperture 500b. The bottom part 580b of the second rod 520b defines a second flange 600b. A second spring 640b is mounted beneath second flange 600b and around the bottom part 580b of second rod 520b. The spring housing 480 ensures that the first 640 and second 640b springs respectively apply an upward force to the first 600 and second 600b flanges and thence respectively to first 520 and second 520b rods, which emerge in a controlled manner through first 500 and second 500b apertures, respectively.

It is to be understood that the present invention is not limited to the embodiments described above, but encompasses any and all embodiments within the scope of the following claims.

I claim:

1. A sinus nerve locator, comprising:
   a drill section of conical shape, said drill section having a top and a bottom end, said drill section comprising a generally elongated first hollow bore, said first hollow bore is disposed inside said drill section and between said top and bottom ends of said drill section, said first hollow bore defining a first aperture in the top of said drill section;

a base member;

a generally elongated first rod, said first rod at least partly located inside said first hollow bore, said first rod having first and second opposite ends;

a means for applying a spring force on said first rod, wherein when a controllable spring tension is applied to one opposite end of said first rod the other opposite end of said first rod is coaxed to emerge through and outward from said first aperture in said top of said drill section;

a generally elongated second hollow bore, said second hollow bore is disposed inside said drill section and between said top and bottom ends of said drill section, said second hollow bore defining a second aperture in the top of said drill section;

a generally elongated second rod, said second rod at least partly located inside said second hollow bore, said second rod having first and second opposite ends; and a second means for applying a spring force on said second rod, wherein when a controllable spring tension is applied to one opposite end of said second rod the other opposite end of said second rod is coaxed to emerge through and outward from said second aperture in said top of said drill section.

2. The sinus nerve locator according to claim 1, wherein the top of said drill section includes a drill tip, and wherein said first and second apertures are separately located proximate to, but not centered on, said drill tip.

* * * * *